(12) United States Patent
Bhanu et al.

(10) Patent No.: US 8,362,042 B2
(45) Date of Patent: Jan. 29, 2013

(54) STABLE R(+)-LANSOPRAZOLE AMINE SALT AND A PROCESS FOR PREPARING THE SAME

(75) Inventors: Manjunath Narayan Bhanu, Maharashtra (IN); Samir Naik, Maharashtra (IN); Arjun Bodkhe, Maharashtra (IN)

(73) Assignee: Watson Pharma Private Limited, Mumbai, Maharashtra (IN)

( * ) Notice: Subject to any disclaimer, the term of this patent is extended or adjusted under 35 U.S.C. 154(b) by 0 days.

(21) Appl. No.: 12/992,034

(22) PCT Filed: May 12, 2009

(86) PCT No.: PCT/IN2009/000279
§ 371 (c)(1),
(2), (4) Date: Nov. 10, 2010

(87) PCT Pub. No.: WO2010/079504
PCT Pub. Date: Jul. 15, 2010

(65) Prior Publication Data
US 2011/0065755 A1 Mar. 17, 2011

(30) Foreign Application Priority Data

May 14, 2008 (IN) .......................... 1036/MUM/2008

(51) Int. Cl.
*A61K 31/4439* (2006.01)
*C07D 401/12* (2006.01)
*A61P 1/04* (2006.01)

(52) U.S. Cl. ..................................... 514/338; 546/273.7
(58) Field of Classification Search .................. None
See application file for complete search history.

(56) References Cited

U.S. PATENT DOCUMENTS

| 4,628,098 | A | 12/1986 | Nohara et al. |
| 6,462,058 | B1 * | 10/2002 | Fujishima et al. ............ 514/338 |
| 6,664,276 | B2 | 12/2003 | Fujishima et al. |
| 7,271,182 | B2 | 9/2007 | Kamiyama et al. |
| 7,285,668 | B2 | 10/2007 | Hashimoto et al. |
| 2003/0181487 | A1 | 9/2003 | Kamiyama et al. |
| 2005/0182099 | A1 * | 8/2005 | Dahlstrom .................... 514/338 |
| 2010/0280077 | A1 | 11/2010 | Naik et al. |

FOREIGN PATENT DOCUMENTS

| CN | 1329003 | 1/2002 |
| EP | 1552833 | 7/2005 |
| JP | 61-50978 | 3/1986 |
| WO | 00/78745 | 12/2000 |
| WO | 2004/083200 | 9/2004 |
| WO | 2006/094904 | 9/2006 |
| WO | 2008/004245 | 1/2008 |
| WO | 2009/087672 | 7/2009 |
| WO | 2010/079504 | 7/2010 |

OTHER PUBLICATIONS

Monk (Physical Chemistry 2004; John Wiley and Sons; p. 241). 1 page.*
Deng et al. (Tetrahedron: Asymmetry 2000, 11, 1729-1732).*
D. Mulhausen, International Preliminary Report on Patentability in PCT/IN2009/000279, Nov. 17, 2010, 5 pages, International Bureau of WIPO, Geneva, Switzerland.
Database WPI Week 2002, Thomson Scientific, London, GB; AN 2002-242372, XP002529611.
S. Lewis, International Search Report in PCT/IN09/00279, Jul. 19, 2010, 5 pages, European Patent Office, Netherlands.
S. Lewis, Written Opinion of the International Searching Authority in PCT/IN09/00279, Jul. 19, 2010, 4 pages. European Patent Office, Netherlands.
P.L. Gould, "Salt Selection for Basic Drugs", International Journal of Pharmaceutics, 1986, vol. 33, pp. 201-217.
Mulhausen, D., International Preliminary Report on Patentability in PCT/IN2008/000842, Jun. 22, 2010, 8 pages, International Bureau of WIPO, Geneva Switzerland. This is a co-owned application.
Guspanova, J., Written Opinion of the International Searching Authority, in PCT/IN2008/000842, Jun. 18, 2010, 7 pages, European Patent Office, Munich, Germany. This is a co-owned application.
Guspanova, J., International Search Report in PCT/IN2008/000842, Jun. 15, 2010, 3 pages, European Patent Office, Rijswijk, Netherlands. This is a co-owned application.

* cited by examiner

*Primary Examiner* — Ernst Arnold
(74) *Attorney, Agent, or Firm* — Florek & Endres PLLC

(57) ABSTRACT

A stable R-(+)-lansoprazole alkylamine salt and a process for preparing the salt.

16 Claims, No Drawings

STABLE R(+)-LANSOPRAZOLE AMINE SALT AND A PROCESS FOR PREPARING THE SAME

This application is a U.S. National Stage filing under 35 U.S.C. §371 of International Application No. PCT/IN2009/000279, filed May 12, 2009, which in turn claims priority to Indian Patent Application No. 1036/MUM/2008, filed May 14, 2008

FIELD OF THE INVENTION

The present invention relates to a stable organic salt of (R)-2-[[[3-methyl-4-(2,2,2-trrifluoroethoxy)-2-pyridinyl]methyl]sulfinyl]-1H-benzimidazole, also known as R-(+)-lansoprazole and a process for preparing the same.

BACKGROUND OF THE INVENTION

2-[[[3-methyl-4-(2,2,2-trifluoroethoxy)-2-pyridinyl]methyl]sulfinyl]-1H-benzimidazole, also known as lansoprazole, is disclosed in Japanese patent application No. JP-A-61-50978.

Lansoprazole is a well-known gastric acid secretion inhibitor and is useful as an anti-ulcer agent. Lansoprazole has a chiral sulfur within its molecular structure and, hence, occurs as two optical isomers, R-lansoprazole and S-lansoprazole.

U.S. Pat. No. 6,462,058 B1 discloses a crystal of R-lansoprazole and its use as an anti-ulcer agent. U.S. Pat. Nos. 6,462,058 B1 and 6,664,276 B2 and PCT Patent Publication No. WO 00/78745 A2 all describe methods to obtain crystals of R-lansoprazole. Exemplary methods for such synthesis include:

a) A fractional crystallization method in which a salt between a racemate lansoprazole mixture and an optically active compound [for example, (+)-mandelic acid, (−)-mandelic acid, (+)-tartaric acid, or (−)-tartaric acid] is formed. The resulting salt is separated by fractional crystallization and then subjected to a neutralization process to give a free optical isomer.

b) A chiral column method in which a racemate or a salt is applied to a column for optical isomer separation. In liquid chromatography, for example, optical isomers are separated by adding the racemate to a chiral column (such as the Daicel® series, produced by Daicel Chemical Industries, Ltd.), and eluting in water, a buffer (for example, a phosphate), an organic solvent (for example, hexane, ethanol, methanol, isopropanol, acetonitrile, triethylamine, or mixtures thereof) or mixtures of the foregoing.

c) A diastereomer method in which a racemate and an optically active reagent are reacted to give a diastereomer mixture. The diastereomer mixture is separated to obtain the desired diastereomer, and the optically active reagent is cleaved.

U.S. Pat. Nos. 6,462,058 B1 and 6,664,276 B2 and PCT Patent Publication No. WO 00/78745 A2 also describe the synthesis of various polymorphic forms of R-(+)-lansoprazole. Some of the polymorphic forms described in these references include: a) an amorphous form that is relatively unstable; b) a crystalline anhydrous form; and c) a crystalline sesquihydrate form. These references further provide X-ray powder diffraction characteristics of the crystalline forms of R-(+)-lansoprazole and the use of the crystalline R-(+)-lansoprazole for manufacturing a pharmaceutical composition for the treatment or prevention of a digestive ulcer.

U.S. Pat. Nos. 6,462,058 B1 and 6,664,276 B2 and PCT Patent Publication No. WO 00/78745 A2 also suggest that various salts of R-(+)-lansoprazole may be prepared such as metal salts, salts of organic bases and salts with amino acids. These references fail to provide any examples for preparing such salts.

U.S. Published Patent Application No. 2003/0181487 A1 describes various metal salts of R-(+)-lansoprazole, including the sodium salt, magnesium salt, lithium salt, calcium salt and barium salt as well as processes for manufacturing these metal salts. This published application states that these metal salts could be used in solid form and exhibited good stability characteristics.

Different salt forms of a pharmaceutically active compound can exhibit different bioavailabilty, solubility, color, compressibility, flowability and/or stability with consequent modification of the profiles of toxicological, safety, clinical effectiveness and productive efficiency. Improved drug formulations are consistently sought after for better bioavailability, better processing characteristics and/or better stability. There is also an ongoing need for new or purer forms of existing drug molecules.

SUMMARY OF THE INVENTION

The present invention relates to a stable organic salt of R-(+)-lansoprazole. The present invention preferably is a stable amine salt of R-(+)-lansoprazole. The amine used to prepare the salt may be a primary, secondary or tertiary alkylamine such as a $C_1$ to $C_6$ mono-, di- or tri-alkylamine. The organic salts prepared in accordance with the present invention should be stable under ambient conditions, 25° C. and 60% relative humidity, for at least 1 week or longer. The organic salts prepared in accordance with the present invention should also be solid at room temperature and may be crystalline or amorphous.

The present invention also relates to a process for preparing a stable organic salt form of R-(+)-lansoprazole such as a stable amine salt of R-(+)-lansoprazole. The process will produce a crystalline or amorphous solid.

One embodiment of the present invention relates to a solid, stable $C_1$ to $C_6$ mono amine salt of R-(+)-lansoprazole, such as the butylamine salt of R-(+)-lansoprazole, and a process for preparing the same.

According to another aspect, the present invention relates to a process for preparation of stable organic salts of R-(+)-lansoprazole, which includes:

i) Optical resolution of racemic lansoprazole by the formation of host-guest inclusion complexes via selectively and reversibly including chiral guest molecules in the host lattices of chiral molecules;

ii) Resolving lansoprazole with 2,2'-dihydroxy-1,1'-binaphthyl (BINOL) as the chiral host, by forming the inclusion complex in a suitable solvent system such as a mixture of toluene and hexane;

iii) Crystallizing the inclusion complex from a suitable solvent system such as a mixture of toluene and hexane to enrich the R-isomer to more than 97% enantiomeric excess ("e.e."), otherwise known as optical purity;

iv) Cleaving the R-(+)-lansoprazole-BINOL inclusion complex with a suitable solvent such as an aqueous ammonia solution and then reacting the extract of R-(+)-lansoprazole in an organic solvent with a $C_1$ to $C_6$ alkylamine; and v) Isolating the $C_1$ to $C_6$ alkylamine salt of R-(+)-lansoprazole.

DESCRIPTION OF THE INVENTION

The present invention relates to a stable organic salt f R-(+)-lansoprazole, preferably a stable amine salt of R-(+)- lansoprazole such as a primary, secondary or tertiary alkylamine such as a $C_1$ to $C_6$ mono-, di- or tri-alkylamine. The stable organic salts prepared in accordance with the present invention are solid at room temperature and may be crystalline or amorphous.

Examples of the alkylamines that may be used in the present invention, include methylamine, ethylamine, propylamine, isopropylamine, butylamine, dimethylamine, diethylamine, dipropylamine, diisopropylamine, dibutylamine, trimethylamine, triethyleamine, tripropylamine and disoproylethyleneamine.

One embodiment of the present invention is a stable, solid butylamine salt of R-(+)-lansoprazole. There are four isomers of butyl amine: tert-butylamine, n-butylamine, sec-butyl amine and isobutylamine. The preferred butyl amine is tert-butylamine. Tert-butylamine is also known as: t-butylamine, tertiary butylamine, 2 amino-2-methylpropane, trimethyl aminomethane, dimethylethylamine, 1-aminobutane, 1,1 dimethylethylamine, 2-aminoisobutane, 2-methyl-2-aminopropane, 2-methylpropylamine, 2-methyl-2-propaneamine. Salts of tert-butylamine are sometimes referred to as "erbumine" salts. For example, the tert-butyl amine salt of R-(+)-lansoprazole may be referred to as the erbumine salt of R-(+)-lansoprazole or R-(+)-lansoprazole erbumine.

Unless otherwise stated, the aforementioned alternative names for tert-butylamine, including the erbumine designation, may be used interchangeably and refer to the tert-butylamine salt.

The salts of the present invention may be prepared by any means commonly known in the art. The first step for preparing the stable amine salts in accordance with the present invention is to prepare the R-(+)-lansoprazole base. Methods for preparing the lansoprazole and R-(+)-lansoprazole base are known in the art and described for example in U.S. Pat. Nos. 4,628,098; 6,462,058; 6,664,276; 7,271,182; and 7,285,668.

Once the R-(+)-lansoprazole base is obtained, it may be reacted in the presence of an organic solvent with an alkylamine as previously described. The resulting alkylamine R-(+)-lansoprazole salt may be isolated from the solvent by any suitable means such as extraction, precipitation, crystallization or evaporation.

One embodiment of the present invention comprises preparing the alkylamine salt of R-(+)-lansoprazole, such as the erbumine salt, by optically resolving a racemic mixture of lansoprazole by a "fractional crystallization method". In this embodiment, a salt is formed between the racemic lansoprazole and an optically active compound such as (+)-mandelic acid, (−)-mandelic acid, (+)-tartaric acid, (−)-tartaric acid, (+)-1-phenethylamine or (−)-1-phenethylamine. The salt is then separated by fractional crystallization and subjected to a neutralization process giving R-(+)-lansoprazole. The R-(+)-lansoprazole is then reacted with an alkylamine, such as tert-butylamine, to obtain the R-(+)-lansoprazole alkylamine salt.

Another embodiment of the present invention comprises preparing the alkylamine salt of R-(+)-lansoprazole by a "chiral column method". In this embodiment, a racemic mixture of lansoprazole is supplied to a chiral column for optical separation of the lansoprazole isomers. The chiral column may be a column used in liquid chromatography or gas chromatorgraphy apparatus. Examples of liquid chromatography chiral columns are ENANTIO-OVM (produced by Tosoh Corporation) or the DAICEL CHIRAL series (produced by Daicel Corporation). An example of a gas chromatography chiral column is CP-Chirasil-DeX CB (produced by GL Science). The R-(+)-lansoprazole obtained from the chiral column is then reacted with an alkylamine, such as tert-butylamine, to obtain a R-(+)-lansoprazole alkylamine salt.

A further embodiment of the present invention comprises preparing the alkylamine salt of R-(+)-lansoprazole by a "diastereomer method". In this embodiment, a racemic mixture of lansoprazole is reacted with an optically active reagent (preferably at the 1-position of the benzimidazole group) to give a diastereomer mixture. Examples of suitable optically active reagent materials include a-methoxy-a-(trifluoromethyl)phenyl acetic acid [MTPA], (−)-menthoxyacetic acid, and (1R-endo-2-(chloromethoxy)-1,3,3-trimethylbicyclo[2,2,1]heptane. The diastereomer mixture is then subjected to conventional separation means such as fractional recrystallization or chromatography to obtain purified forms of the diastereomers. The purified diastereomer is then subjected to a chemical reaction to remove the optically active reagent and obtain R-(+)-lansoprazole. The R-(+)-lansoprazole is then reacted with an alkylamine, such as tert-butylamine, to obtain R-(+)-lansoprazole alkylamine salt.

It is contemplated in accordance with the present invention that R-(+)-lansoprazole alkylamine salt obtained from any of the above described processes may be prepared by treating crystalline R-(+)-lansoprazole with the alkyamine, and in particular tert-butylamine, in an organic solvent to obtain the desired alkylamine salt, such as the erbumine salt. The amount of alkylamine used to prepare the R-(+)-lansoprazole salt should be in a molar excess to the amount of R-(+)-lansoprazole present in the reaction mixture. An embodiment of the present invention employs a ratio of R-(+)-lansoprazole to alkylamine in the salt forming reaction of about 1 mole R-(+)-lansoprazole to about 1.5 moles alkylamine to about 1 mole R-(+)-lansoprazole to about 5 moles alkylamine, preferably about 1 mole R-(+)-lansoprazole to about 2 moles alkylamine to about 1 mole R-(+)-lansoprazole to about 4 moles alkylamine.

One aspect of the present invention that is useful in preparing alkylamine salts of R-(+)-lansoprazole, and the erbumine salt in particular, comprises the following steps:

a) Treating racemic lansoprazole with R-(+)-BINOL (R-(+)-2,2'-dihydroxy-1,1'-binaphthyl) in a-suitable solvent to form the inclusion complex of R-(+)-lansoprazole with R-(+)-BINOL;

b) Removing the inclusion complex of R-(+)-lansoprazole with R-(+)-BINOL prepared in step (a) from the solvent and adding a mixture of organic solvents, such as toluene and hexane, to the inclusion complex at a temperature of about 10° C. to about 40° C., more preferably about 20° C. to 25° C.;

c) Crystallizing the R-(+)-lansoprazole-R-(+)-BINOL inclusion complex from the mixture of organic solvents at a temperature of about −5° C. to about 30° C., more preferably about 0° C. to about 10° C. and most preferably about 0° C. to about 5° C.;

d) Enriching the R-(+)-lansoprazole-R-(+)-BINOL inclusion complex, preferably by recrystallization from a suitable solvent system such as a mixture of toluene and hexane to give R-(+)-lansoprazole-R-(+)-BINOL inclusion complex having a chiral purity of more than about 97% e.e.;

e) Cleaving the enriched R-(+)-lansoprazole-R-(+)BINOL complex by treating with a suitable solvent system such as liquor ammonia at about 0° C. to about 50° C., preferably about 20° C. to about 45° C., and more preferably about 25° C. to about 35° C., to obtain a mixture of R-BINOL and R-(+)-lansoprazole in aqueous ammonia solution;

f) Separating out R-BINOL from R-(+)-lansoprazole; and
g) Isolating R-(+)-lansoprazole from the aqueous ammonia solution by adjusting the pH of the ammonia solution from about 7 to about 10, more preferably about 8 to about 9.5, and most preferably about 9 to about 9.3, and filtering the isolated R-(+)-lansoprazole.

The solvent used to form the inclusion complex of R-(+)-lansoprazole with R-(+)-BINOL in step (a) is preferably an organic solvent, preferably a halogenated organic solvent such as methylene dichloride. Once the inclusion complex of R-(+)-lansoprazole with R-(+)-BINOL is prepared, the solvent used in the preparation step (a) is removed by conventional techniques such as by distillation or evaporation. If the preparation solvent of step (a) is methylene dichloride, the preferred removal method is by distillation.

Once the preparation solvent of step (a) is removed, a mixture of organic solvents is added to the inclusion complex. The mixture of organic solvents preferably is a mixture of aromatic and aliphatic solvents such as toluene and hexane. The ratio of aromatic to aliphatic in the mixture should range from about 1:1 to about 5:0.5, preferably about 2:1 to about 5:1 and most preferably about 4:1.

The enrichment of the R-(+)-lansoprazole-R-(+)-BINOL inclusion complex can be performed by any conventional methods, preferably by one or more recrystallizations from a suitable solvent system. A suitable solvent system is preferably a mixture of organic solvents. The preferred mixture comprises a combination of aromatic and aliphatic solvents such as toluene and hexane. The ratio of aromatic to aliphatic in the mixture should range from about 1:1 to about 5:0.5, preferably about 2:1 to about 5:1, and most preferably about 4:1. Once the enrichment step is completed the R-(+)-lansoprazole-R-(+)-BINOL inclusion complex should have a purity of at least 97% and preferably at least 98%.

After the R-(+)-lansoprazole-R-(+)-BINOL inclusion complex is enriched, the complex is cleaved using a suitable solvent cleaving system. A suitable solvent cleaving system may contain water and an amine compound. A preferred solvent cleaving system is an aqueous ammonia solution. Once the R-(+)-lansoprazole and R-(+)-BINOL have been cleaved, the R-(+)-lansoprazole and BINOL components are separated by methods known in the art. In one embodiment of the present invention, the R-(+)-lansoprazole and the BINOL components are separated by solvent extraction. The preferred solvent for the extraction is methyl tertiary butyl ether.

The R-(+)-lansoprazole obtained from the above process may be then suspended or dissolved in a suitable solvent followed by the addition of the desired alkylamine. The solvent may be an organic solvent such as an ester containing solvent. Examples of ester solvents that may be useful include methyl acetate, ethyl acetate, propyl acetate, butyl acetate and mixtures of the foregoing. The suspension or solution should be at a temperature of about 10° C. to about 60° C., preferably about 15° C. to about 45° C. After the alkylamine salt is added and allowed to react with the R-(+)-lansoprazole, the reaction mixture is cooled to less than 10° C., preferably about 5° C. or less, until crystals of the R-(+)-lansoprazole alkylamine salt are obtained. The R-(+)-lansoprazole alkylamine salt crystals are filtered, washed and dried.

The R-(+)-lansoprazole alkylamine salts prepared in accordance with the present invention may be mixed with at least one additional conventional pharmaceutical excipient to prepare a pharmaceutical dosage form such as a tablet, capsule or solution.

The R-(+)-lansoprazole alkylamine salts prepared in accordance with the present invention are stable for at least one week when stored in an open glass container at 25° C. and 60% relative humidity. The stability is determined by measuring the color change and residual content of the R-(+)-lansoprazole alkylamine salt following storage. After storage, the sample should contain at least 85% of the initial salt concentration, preferably at least 90% of the initial salt concentration, and most preferably at least 95% of the initial salt concentration.

The following are provided as examples of the invention and are not intended to be limiting.

EXAMPLES

Example 1

Resolution of (R)-2-[[[3-methyl-4-(2,2,2-trifluoroethoxy)-2-pridinyl-1]methyl]sulfinyl]-1H-benzimidazole (R-(+)-lansoprazole) from racemic Lansoprazole 2-[[[3-methyl-4-(2,2,2-trifluoroethoxy)-2-pridinyl-1]methyl]sulfinyl]-1H-benzimidazole (racemic lansoprazole) (200 gm, 0.542 moles) and R-(+)-BINOL (232.52 gm, 0.813 moles) were dissolved in methylene dichloride (7 L) at room temperature in a 10 L flask and heated to 35-40° C., under stirring, to obtain a clear solution. The reaction mixture was concentrated under vacuum below 35° C. until the volume of the reaction mixture was approximately 5-6 times with respect to lansoprazole. Toluene (5760 ml) was charged to the reaction mixture, which was cooled to about 20-25° C. n-Hexane (1440 ml) was then added and the temperature was maintained between 20° C. and 25° C. The reaction mixture was then cooled to 0-5° C. and stirred at this temperature for 12 hours. The crystallized product was filtered and washed with n-hexane and suck-dried to obtain 230 gm of crude R-(+)-lansoprazole-R-(+)-BINOL inclusion complex.

Purification of Crude Complex

The crude R-(+)-lansoprazole-R-(+)-BINOL inclusion complex was dissolved in 3000 ml methylene dichloride and concentrated under vacuum maintaining the temperature below 35° C. until the volume of the reaction mixture was about 5-6 times with respect to lansoprazole. Toluene (5760 ml) was charged to reaction mixture and the reaction mixture was cooled to about 20-25° C. n-Hexane (1440 ml) was added, maintaining the temperature between 20° C. and 25° C. The reaction mixture was then cooled to 0-5° C. and stirred at this temperature for 12 hours. The crystallized product was filtered and washed with n-hexane. The wet product was dried at 40° C. under vacuum to obtain 185 gm of pure R-(+)-lansoprazole-R-(+)-BINOL inclusion complex.

Chiral purity by HPLC>97% e.e.
Yield: 92.55% w/w

Example 2

Preparation of Tertiarybutylamine salt of (R)-2-[[[3-methyl-4-(2,2,2-trifluoroethoxy)-2-pridinyl-1]methyl]sulfinyl]-1H-benzimidazole (R-(+)-Lansoprazole Erbumine)

185 gm of the pure R-(+)-lansoprazole-R-(+)-BINOL inclusion complex obtained in Example 1 was dissolved in methanol (92.5 ml) and liquor ammonia (925 ml) at 40-45° C.

Methyl tertbutyl ether (MTBE) (925 ml) was added to the reaction mixture at 40-45° C. and stirred for 10 min to get a clear solution. The organic layer was separated and extracted with liquor ammonia twice (462.5 ml×2 times) at 40-45° C. and the organic layer was again separated. All of the aqueous layers were collected and washed twice with MTBE (462.5 ml×2) at 40-45° C. The aqueous layer was separated and ethyl acetate (925 ml) was charged at room temperature, and the pH of the aqueous layer was adjusted to 6 using acetic acid. The ethyl acetate layer was separated and again the aqueous layer was extracted twice with ethyl acetate (450 ml). All the ethyl acetate layers were combined together and washed with a 20% brine solution (450 ml). The ethyl acetate layer was separated and dried over sodium sulfate. The ethyl acetate extract was concentrated under vacuum below 40° C. to keep about 300 ml of ethyl acetate in the reaction mass. 19.84 gm of tertiary butylamine was added slowly to the reaction mixture at 20-30° C. under stirring and maintaining a nitrogen atmosphere in the reaction vessel. The reaction mixture was cooled to 0-5° C. and stirred at this temperature for 2 hours to crystallize out the tertiary butylamine salt of R-(+)-lansoprazole. The crystalline product was filtered under nitrogen blanket and washed with 50 ml chilled ethyl acetate. The wet product was sucked-dried for 30 minutes under nitrogen blanket and then further dried at 40-45° C. under vacuum for about 5 hours. The weight of the R-(+)-lansoprazole erbumine salt was about 40 mg. HPLC purity was >99.5%. Chiral purity by HPLC>99% e.e. and SOR=130° C.

Example 3

Preparation of Tertiarybutylamine salt of (R)-2-[[[3-methyl-4-(2,2,2-trifluoroethoxy)-2-pridinyl-1]methyl]sulfinyl]-1H-benzimidazole (R-(+)-Lansoprazole Erbumine)

10 gm of a crystalline sample of R-(+)-lansoprazole was suspended in 70 ml of ethyl acetate, maintaining a nitrogen atmosphere in the reaction vessel at 20-30° C. 4.96 g of tertiary butylamine was slowly added to the reaction mixture at 20-30° C. and the reaction mixture was cooled to 0-5° C. and stirred at 0-5° C. for 2 hours. The crystalline product was filtered and washed with 10 ml of chilled ethyl acetate. The wet product was suck-dried for 30 minutes under nitrogen blanket and then further dried at 40-45° C. under vacuum for about 5 hours. The weight of the R-(+)-lansoprazole erbumine salt was about 10 mg.

We claim:

1. A process for preparing stable R-(+)-lansoprazole butylamine salt comprising the following steps:
    (a) treating racemic lansoprazole with R-(+)-2,2'-dihydroxy-1,1'-binaphthyl ("R-(+)-BINOL") in a suitable solvent to form the inclusion complex of R-(+)-lansoprazole with R-(+)-BINOL;
    (b) removing the inclusion complex of R-(+)-lansoprazole with R-(+)-BINOL prepared in step (a) from the solvent and adding a mixture of organic solvents;
    (c) crystallizing the R-(+)-lansoprazole-R-(+)-BINOL inclusion complex from the mixture of organic solvents;
    (d) enriching the R-(+)-lansoprazole-R-(+)-BINOL inclusion complex to obtain a purity of more than about 97% e.e.;
    (e) cleaving the enriched R-(+)-lansoprazole-R-(+)-BINOL inclusion complex;
    (f) separating the R-(+)-BINOL and R-(+)-lansoprazole;
    (g) isolating the R-(+)-lansoprazole; and
    (h) reacting the R-(+)-lansoprazole with a butylamine to form a stable R-(+)-lansoprazole butylamine salt.

2. The process of claim 1, wherein the mixture of organic solvents is a mixture of an aromatic and an aliphatic solvent.

3. The process of claim 2, wherein the mixture of solvents is toluene and hexane.

4. The process of claim 2 wherein the ratio of aromatic to aliphatic solvent is about 1:1 to about 5:0.5.

5. The process of claim 4 wherein the ratio of aromatic to aliphatic solvent is about 2:1 to about 5:1.

6. The process of claim 5 wherein the ratio of aromatic to aliphatic solvent is about 4:1.

7. The process of claim 1, wherein the enriched (R)-lansoprazole R-(+)-BINOL inclusion complex is cleaved with an aqueous ammonia solution to give R-(+)-lansoprazole.

8. The process of claim 1 wherein the butylamine is tert-butylamine.

9. The process of claim 1 wherein the R-(+)-lansoprazole-R-(+)-BINOL inclusion complex is enriched to obtain a purity of at least 98% e.e.

10. The process of claim 1 wherein the enriched R-(+)-lansoprazole-R-(+)-BINOL inclusion complex is cleaved at a temperature of about 0° C. to about 50° C.

11. The process of claim 1 wherein the enriched R-(+)-lansoprazole-R-(+)-BINOL inclusion complex is cleaved at a temperature of about 20° C. to about 45° C.

12. The process of claim 1 wherein the enriched R-(+)-lansoprazole-R-(+)-BINOL inclusion complex is cleaved at a temperature of about 25° C. to about 35° C.

13. A solid R-(+)-lansoprazole butylamine salt produced according to the process of claim 1.

14. The solid R-(+)-lansoprazole butylamine salt as defined in claim 13 wherein the butylamine is tert-butylamine.

15. The solid R-(+)-lansoprazole butylamine salt as defined in claim 13 wherein the butylamine salt is a crystalline material.

16. A pharmaceutical dosage form comprising an R-(+)-lansoprazole butylamine salt according to claim 13 and at least one additional pharmaceutically acceptable excipient.

* * * * *